United States Patent [19]

Scott et al.

[11] Patent Number: 4,722,328

[45] Date of Patent: Feb. 2, 1988

[54] CHIROPRACTIC MANIPULATION TABLE

[75] Inventors: Gerald R. Scott, Elmhurst; Frank P. Kowalski, Des Plaines, both of Ill.

[73] Assignee: Standex International, Salem, N.H.

[21] Appl. No.: 780,304

[22] Filed: Sep. 26, 1985

[51] Int. Cl.⁴ .................................................. A61F 5/01

[52] U.S. Cl. ............................................ 128/74; 5/61; 5/66; 269/325

[58] Field of Search ................................ 269/323-325; 5/61-63, 66; 128/33, 71-74

[56] References Cited

U.S. PATENT DOCUMENTS

| | | | |
|---|---|---|---|
| 385,545 | 7/1888 | Cowles | 269/324 |
| 1,062,489 | 5/1913 | McManis et al. | 128/74 |
| 1,386,901 | 8/1921 | Schreiner | 128/73 |
| 1,427,004 | 8/1922 | McManis | 128/73 |
| 1,453,013 | 4/1923 | Koenigkramer | 128/74 |
| 1,642,158 | 9/1927 | Kubista | 128/71 |
| 1,686,979 | 10/1928 | McManis | 128/33 |
| 2,208,502 | 7/1940 | Kjelgaard | 128/72 |
| 2,693,987 | 11/1954 | Wall | 269/323 |
| 3,176,975 | 4/1965 | Burzlaff | 269/325 |
| 4,025,972 | 5/1977 | Adams | 5/63 |
| 4,118,811 | 10/1978 | Degen | 5/62 |

FOREIGN PATENT DOCUMENTS

| | | | |
|---|---|---|---|
| 466091 | 10/1951 | Italy | 5/61 |
| 2071612 | 9/1981 | United Kingdom | 5/66 |

*Primary Examiner*—Clyde I. Coughenour
*Attorney, Agent, or Firm*—Mason, Kolehmainen, Rathburn & Wyss

[57] ABSTRACT

A table for supporting a patient lying in a generally horizontal position for chiropractic manipulation includes a base projecting upwardly from the floor to a convenient working level and a pivotally mounted thoracic support section for supporting the thorax of the patient which is adjustable about an axis generally corresponding to the patient's spinal axis. The table includes a caudal section supportively connected to the base with ball joints permitting movement of the patient's legs in lateral caudal flexion from side to side about a generally vertical yaw axis and flexion movement about a laterally extending horizontal pitch axis in a vertical direction between upwardly sloping and downwardly sloping positions. A support cushion is mounted for rotation on the caudal section between a range of selected rotational positions about a longitudinal roll axis to accomplish caudal rotation of the patient. A leaf spring and adjustment assembly compensate for a patient's weight. Lock means and height adjustment means are provided.

59 Claims, 24 Drawing Figures

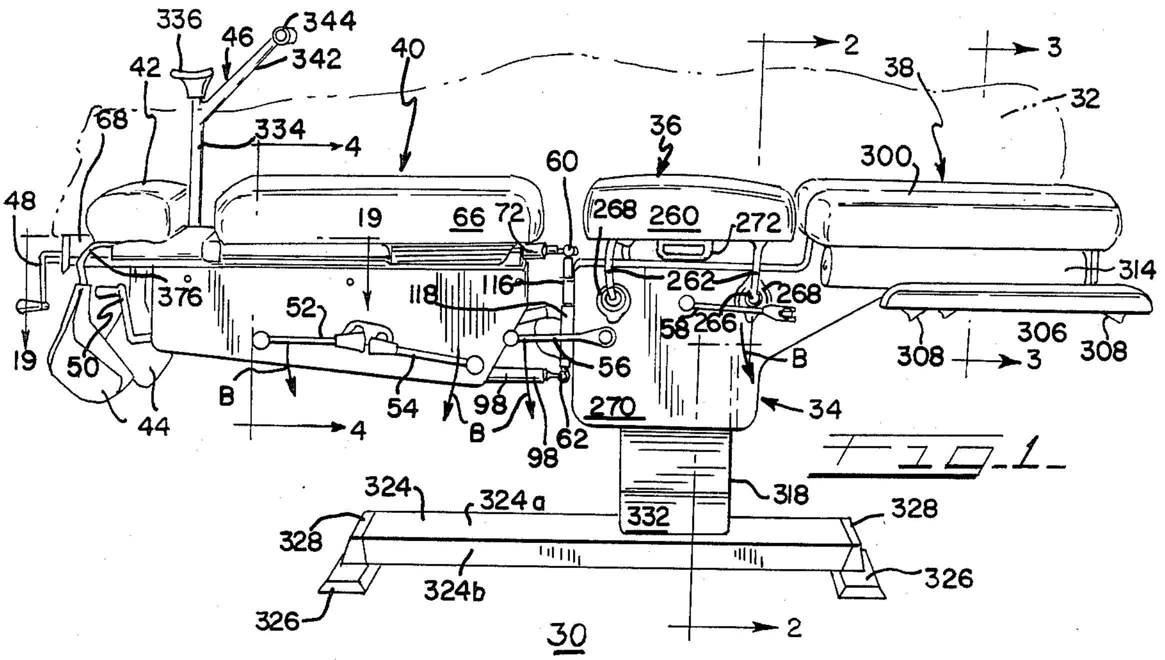
FIG. 1
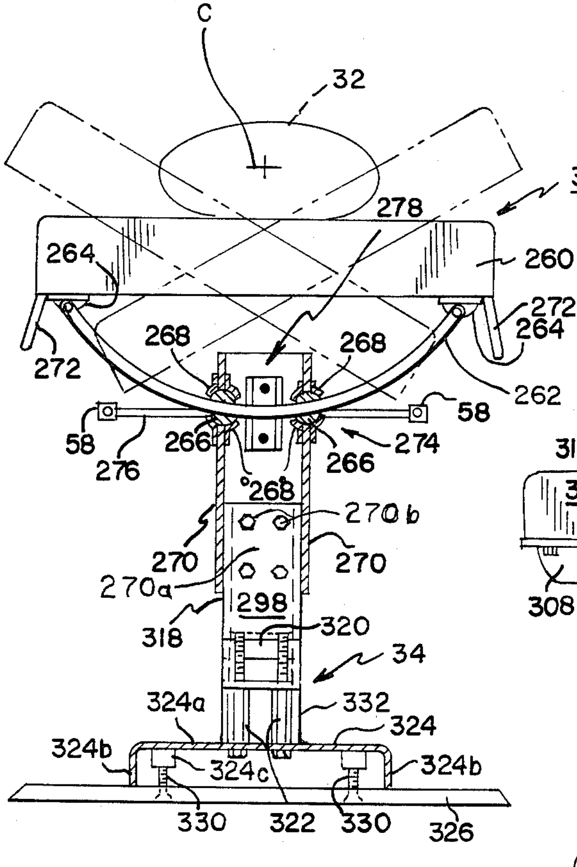
FIG. 2
FIG. 3
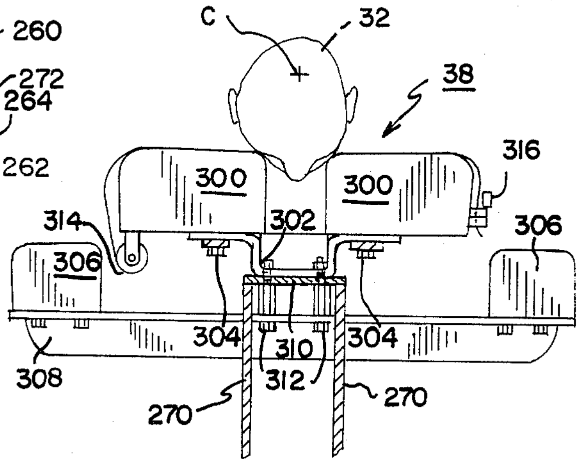
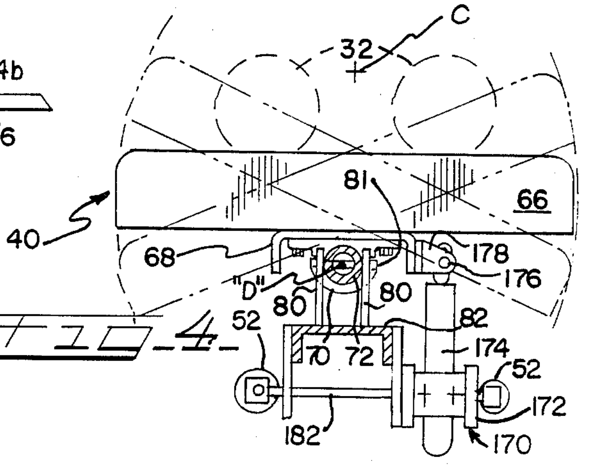
FIG. 4

FIG. 8
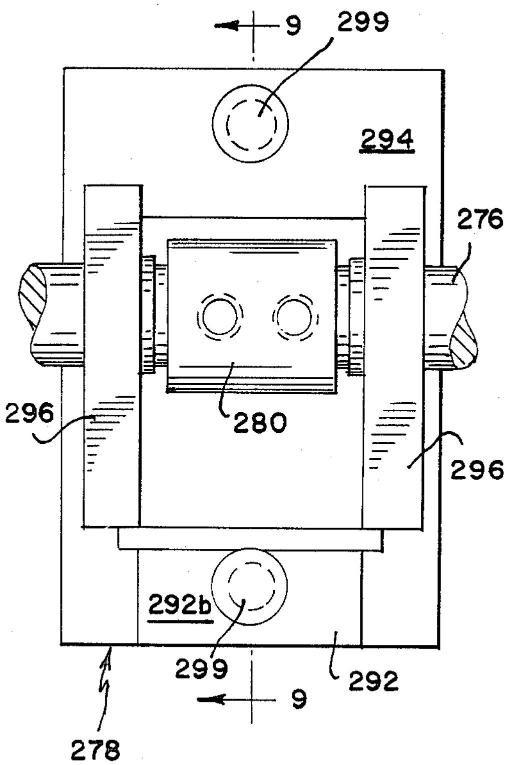
FIG. 9
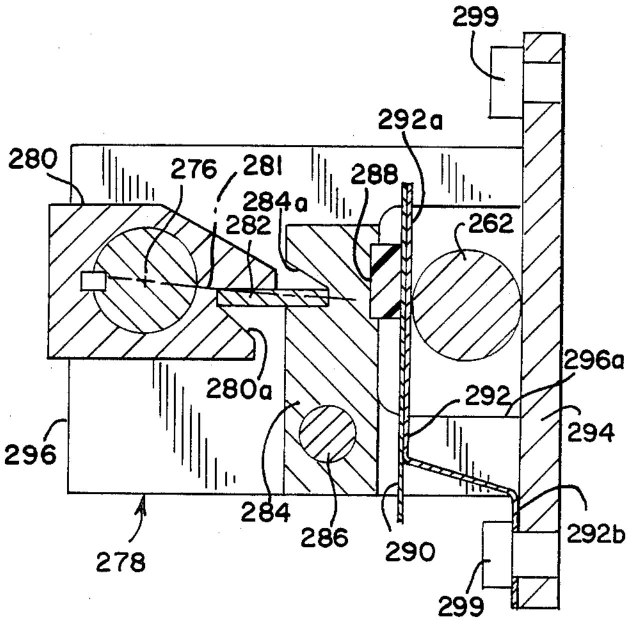
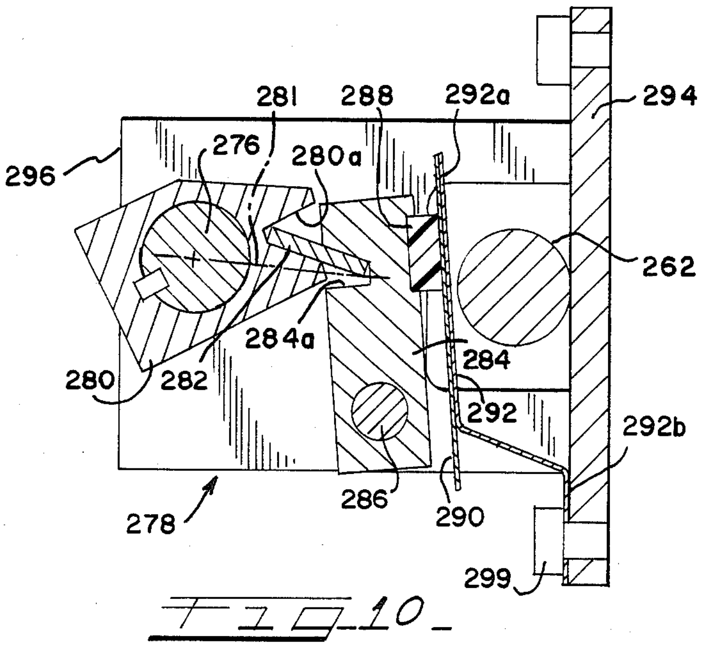
FIG. 10

CHIROPRACTIC MANIPULATION TABLE

BACKGROUND OF THE INVENTION

1. Field of the Invention

The present invention relates to a new and improved chiropractic manipulation table and more particularly to a table for supporting a patient lying in a generally horizontal position for manipulation by a chiropractor standing on either side of the table. Particularly, the new and improved table is capable of accomodating thoracic rotational adjustment of a patient's thorax about a roll axis extending generally longitudinally of the patient's spine, along with vertical movements in flexion distraction of the patient's caudal section about a lateral pitch axis extending generally through the pelvic region of the hips of the patient, caudal roll adjustment, and lateral flexion manipulation about a vertical yaw axis wherein the patient lower torso are manipulated laterally from side to side.

2. Description of the Prior Art

Over the years a number of different chiropractic patient treatment tables have been developed and one such table is known as the Lloyd Galaxy McManis Table offered for sale by the Lloyd Table Company of Lisbon, Iowa. Another line of tables known as Back Specialists Tables have been marketed by The Davis Equipment Company and a Model 1000 employs coil springs for biasing movements of a leg supporting cushion of the table relative to a main table portion supporting the thorax of the patient. A table known as the Barnes Flexion-Distraction Table has been provided for treatment of lower back pain and spine adjustment offered by Custom Tool, Inc. of Fort Wayne, Ind. The Barnes Table employs coil springs in biasing engagement with a leg supporting cushion assembly of the table.

OBJECTS OF THE INVENTION

It is an object of the present invention to provide a new and improved patient treatment table and more particularly to provide a new and improved table for supporting a patient lying in a generally horizontal position for manually controlled chiropractic manipulation.

It is another object of the present invention to provide a new and improved patient treatment table which is especially suited for rotational sublaxation, motion palpitation and scoliosis treatment.

Another object of the present invention is to provide a new and improved patient treatment table for chiropractic manipulation of a patient in a horizontal lying position thereon which has positive locking mechanisms and component controls which are readily accessible from opposite sides of the table for allowing different sections of the table to be locked in selected positions for different degrees of derotation, or released for flexion distraction or lateral flexion manipulation.

Another object of the present invention is to provide a new and improved patient treatment table which employs a detachable assist bar for providing easier flexion distraction and lateral flexion manipulation of a patient by a chiropractic practitioner.

Yet another object of the present invention is to provide a new and improved chiropractic treatment table which is adjustable to several fixed working height ranges varying from 20 inches to 32 inches above the floor level.

Another important object of the present invention is to provide a new and improved patient treatment table employing a novel leaf spring assembly for providing essentially constant caudal flexion distraction resistance wherein the amount of externally applied force required of a chiropractor during flexion treatment is substantially uniform over a relatively wide range of angular displacements.

Still another object of the present invention is to provide a new and improved patient treatment table having a novel ankle support system and an ankle cuff assembly for positively securing the ankles of a patient in an in-line condition during manipulation.

Still another object of the present invention is to provide a new and improved patient treatment table of the character described which is easily adjustable to accomodate patients of different height and which provides a spring tension adjustment system for the automatic leveling a caudal support section of the table in relation to a thoracic support section so as to accomodate a wide range of patient weights.

BRIEF SUMMARY OF THE PRESENT INVENTION

The foregoing and other objects and advantages of the present invention are accomplished in an illustrated embodiment of a new and improved patient treatment table specially designed for supporting a patient lying in a generally horizontal position for manually controlled chiropractic manipulation. The table includes a base structure extending upwardly of the floor level to provide a convenient working level for a chiropractor. The base provides support for a pivotal thoracic section which is rotatable through a range of angular positions about a longitudinal axis generally aligned along the spinal center line (axis) of a patient lying on the table. A caudal support section is provided for manipulating the lower torso of a patient relative to the thoracic section during controlled flexion distraction about a lateral pitch axis extending generally across the patient's hips. A ball joint system is provided for interconnecting the caudal support section and the base to provide lateral flexion of the patient's lower torso about a generally vertical axis from side to side in addition to caudal flexion distraction in a vertical direction up and down. A novel leaf spring assembly is provided to resist caudal flexion distraction at a relatively constant force value independent of the angular displacement when manipulating the caudal support section in a vertical direction about the lateral pitch axis. The spring assembly insures that a substantially constant value of externally applied manipulating force is required from the chiropractor in order to pivot a patient's lower torso through a relatively wide angular range of vertical position inflexion distraction between an upwardly extending position and a lower sloping position relative to the patient's thorax.

The table includes a spring adjustment assembly for compensating for different weights of patients by adjusting the leaf spring assembly to align the caudal support section in a generally level relationship to the thoracic support section. A novel ankle support section is provided to accommodate patients of different heights and to positively secure the ankles of a patient on the caudal support section for manipulation of the lower torso. New and improved over-center type toggle locks are provided for selectively locking and releasing operating components of the table in selected positions and the locking mechanisms are adapted to be unlocked by downward movement of control handles which are duplicated on both sides of the table so that a chiropractor need not move around the end of the table from one side to the other during treatment. In addition, a novel detachable assist bar or handle is provided for improving the chiropractor's working position for the flexion distraction treatment.

BRIEF DESCRIPTION OF THE DRAWING

For a better understanding of the present invention reference should be had to the following detailed description taken in conjunction with the drawings, in which:

FIG. 1 is a side elevational view of a new and improved patient treatment table constructed in accordance with the features of the present invention and illustrating in dotted lines the outline of a patient lying face down in horizontal position on the table ready for manipulative treatment;

FIG. 2 is a vertical transverse cross-sectional view taken substantially along line 2—2 of FIG. 1;

FIG. 3 is a vertical transverse cross-sectional view taken substantially along lines 3—3 of FIG. 1;

FIG. 4 is a fragmentary transverse cross-sectional view taken substantially along lines 4—4 of FIG. 1;

FIG. 5B is a fragmentary side elevational view similar to FIG. 5 illustrating the candual support section in a downwardly sloped position;

FIG. 8 is a vertical elevational view of an over-center, toggle locking mechanism in accordance with the present invention provided for locking the pivotal thoracic support section of the table in a selected rotational position for derotational treatment of a patient;

FIG. 9 is a transverse cross-sectional view taken substantially along lines 9—9 of FIG. 8 illustrating the locked position;

FIG. 10 is a transverse cross-sectional view similar to FIG. 9 illustrating the locking mechanism in an unlocked position;

DESCRIPTION OF A PREFERRED EMBODIMENT OF THE INVENTION

Figure 22:
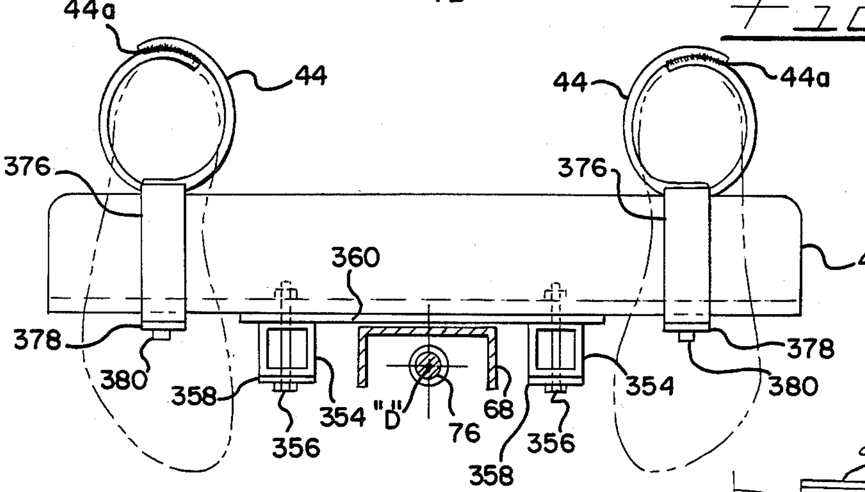
FIG. 22 is an end elevational view looking in the direction of arrows 22—22 of FIG. 19 and illustrating the ankle attaching cuffs in accordance with the present invention.

Referring now more particularly to the drawings, therein is illustrated a patient treatment table 30 for supporting a patient 32 lying in a generally horizontal position face down for manually controllable chiropractic manipulation. The table 30 includes a central support base 34 on which is mounted a pivotal thoracic support section 36 (FIGS. 1 and 2) for supporting the thorax of the patient. The support base 34 also supports a head support section 38 adjacent a right hand end portion or head end of the table as illustrated in FIG. 1. An opposite or foot end of the table 30 includes a caudal or leg support section 40 also interconnected with and supported from the base 34. The caudal section includes an ankle support cushion 42 and a pair of ankle cuffs 44 attached to the cushion for securing the ankles of a patient in place as shown in FIG. 22. For greater ease in the caudal manipulation of a patient on the table for treatment in flexion distraction about a generally horizontal pitch axis extending transversely of the patient's spinal cord across the hip region, the table is provided with a detachable assist bar 46 securable to support structure of the caudal section between the legs of the patient as shown in detail in FIGS. 16, 17 and 18. A caudal support cushion 66 is movable and adjustable in a longitudinal direction along the central axis C—C of the table as indicated by the arrow A (FIG. 19) to accommodate patients of different heights and a rear caudal crank 48 is provided for controlling the amount of adjustment. The table is also provided with a spring tension adjustment crank 50 positioned below and inwardly of the rear caudal crank 48 for adjusting the level of table flexion resistance force in order to accommodate patients of differing weights.

Each side of the table 30 is provided with a caudal rotation lock lever 52, a caudal flexion lock lever 54, a caudal swing lock lever 56 and a pivotal thoracic lock lever 58. Duplication of each of these levers on an opposite side of the table provides for easy access and control of the chiropractic manipulation and treatment of a patient from either side of the table without the necessity of having to walk around an end of the table, merely to lock or unlock a particular component control lever. As illustrated, the respective levers 52, 54, 56 and 58 each have control knobs adjacent the outer end and the levers are shown in a generally horizontal, locking position and are unlocked by downward movement of the outer end portions of the lever as indicated by the arrows B. Downward unlocking of the levers provides ease of operation for the chiropractor when treating and manipulating a patient.

Figure 5:
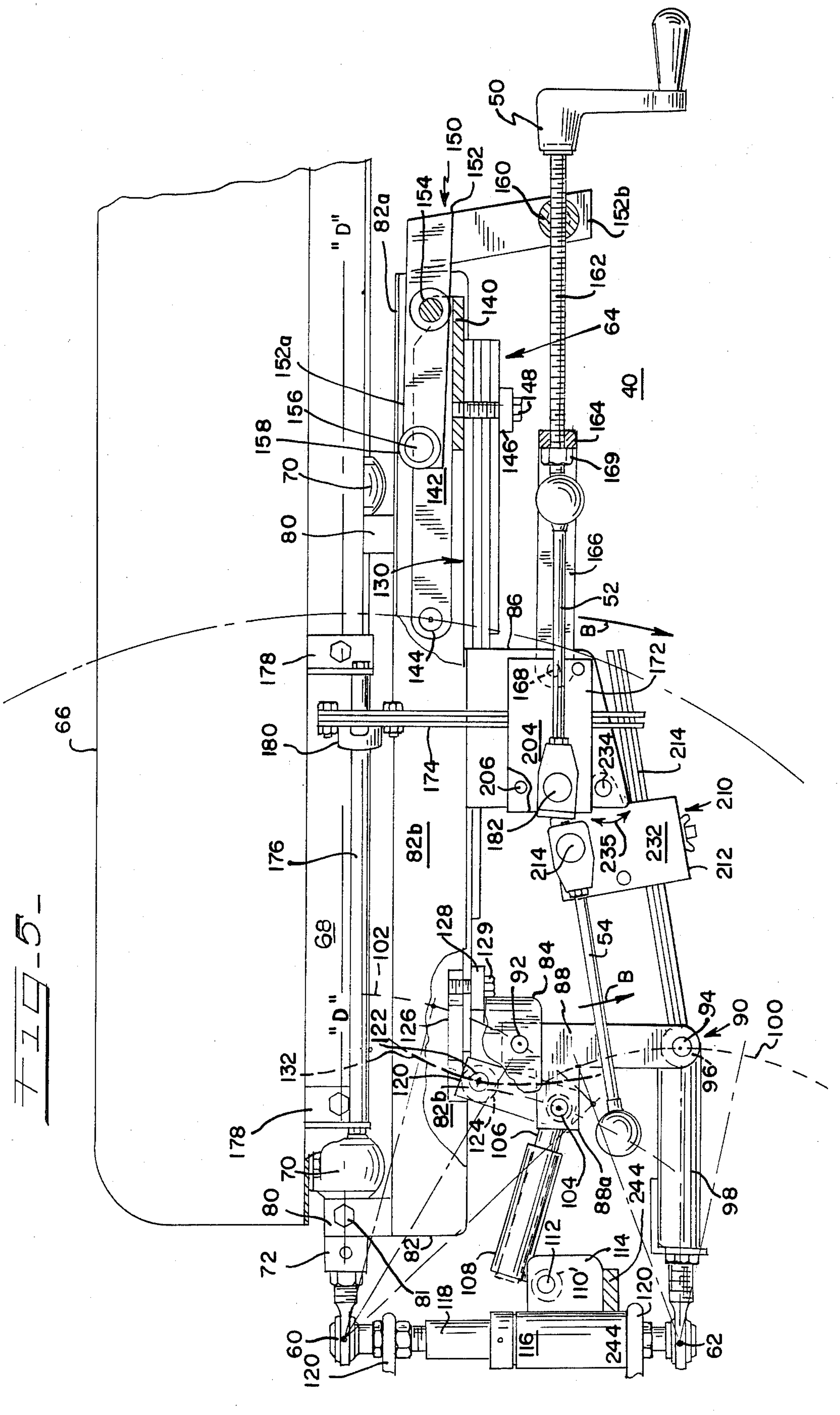
FIG. 5 is a fragmentary, side elevational view with portions broken away and in section for clarity illustrating a caudal support section and leaf spring assembly and spring adjustment control mechanism associated therewith for providing an improved type caudal flexion distraction resistance.
Figures 5A, 6:
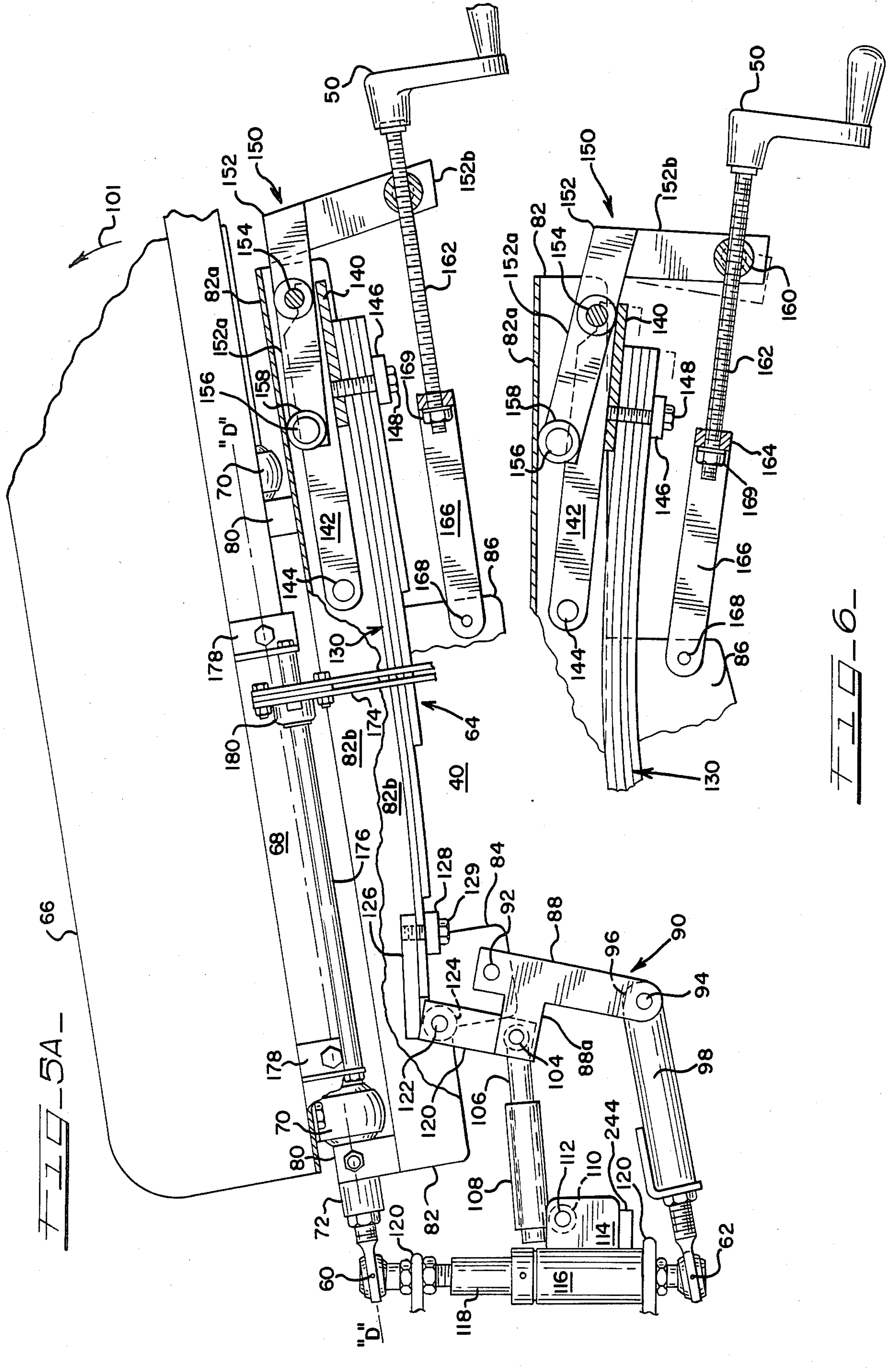
FIG. 5A is a fragmentary side elevational view similar to FIG. 5 illustrating the caudal support section in an upwardly extending position.
FIG. 6 is a fragmentary side elevational view illustrating in detail a leaf spring adjustment assembly for use in compensating for patients of different weight.

In accordance with the present invention, the caudal section 40 is interconnected and supported from the central support base structure 34 by a pair of upper and lower ball joints 60 and 62 which permit the caudal section to pivot upwardly and downwardly in flexion distraction about a generally horizontal, pitch axis extending laterally outwardly of a longitudinal axis of the table, which longitudinal axis is generally aligned with the spinal column of a patient 32 lying on the table. Manipulation of the caudal section between an upper position as shown in FIG. 5A, a level position shown in FIG. 5 and a lower position as shown in FIG. 5B is known as flexion distraction and is useful in treatment of a patient. Lateral pivotal swinging movement of the caudal section about a generally vertically extending yaw axis adjacent the thoracic support section 36 is termed caudal swinging action or lateral flexion.

Figures 15, 16, 17, 18:
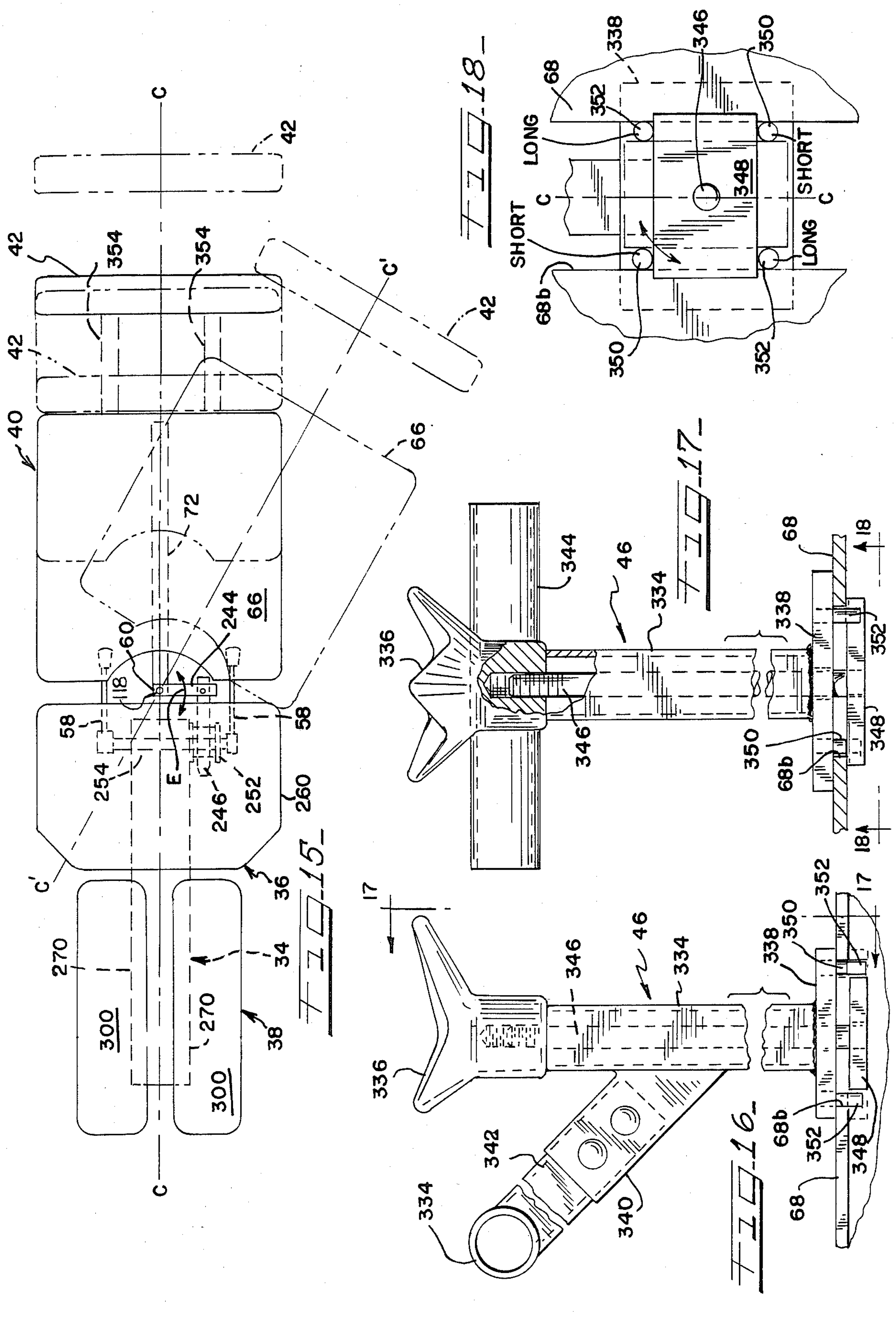
FIG. 15 is a schematic and diagrammatic top plan view of the patient treatment table showing in a phantom view, a lateral flexion position of the caudal support section as it is pivoted about a vertical yaw axis from side to side and illustrating in phantom views several longitudinal adjustment positions of an ankle support for accommodating patients of different height.
FIG. 16 is a side elevational view of a detachable assist bar or handle as secured in position for assisting a practitioner in manipulating a patient during treatment.
FIG. 17 is a cross-sectional view taken substantially along lines 17—17 of FIG. 16.
FIG. 18 is a cross-sectional view taken substantially along lines 18—18 of FIG. 17.

In an embodiment constructed in accordance with the invention, pivotal movement in caudal flexion distraction from the level position of FIG. 5 to an upper position (FIG. 5A) can be accommodated up to an amount of 10° above the horizontal and maximum downward pivotal movement from the level as indicated by FIG. 5B, can be as much as 20° below the horizontal. Referring momentarily to FIG. 15, lateral flexion or swinging movement about the vertical yaw axis extending through the ball joints 60 and 62 can be accommodated up to 25° right or left as indicated by the line C'—C'.

In accordance with the present invention, the caudal section 40 also provides for caudal rotation of up to 18° in either direction (FIG. 4) from a horizontal position about a longitudinal axis D—D of the caudal section spaced below the spinal axis C—C of the patient. As best illustrated in FIG. 2, the pivotal thoracic support section 36 also provides for rotational pivotal movement up to 25° right or left from the horizontal for accommodating thoracic rotation of the patient about the longitudinal axis C—C which is generally aligned with the spinal axis of the patient on the table and which is spaced above the support cushions as will be more fully described hereinafter.

From the foregoing, it will be seen that the patient treatment table 30 provides an extremely useful design for wide ranging chiropractic manipulation including caudal flexion distraction between 10° up and 20° down; lateral caudal flexion between 25° right or left of the center line; axial caudal rotation of up to 18° in either direction about the longitudinal axis D—D of the caudal section (FIG. 4); and thoracic rotation of up to 25° in either direction about a longitudinal axis C—C generally coincident with a patient's spinal cord.

In general, most treatment is accomplished with one or more levers in the locked position such as the caudal rotation lock lever 52 and the pivotal thoracic lock lever 58 after a desired amount of caudal or thoracic rotation is selected. The caudal flexion distraction lock lever 42 and the caudal swing lock lever 56 may be unlocked together for permitting simultaneous movement in caudal flexion distraction in combination with caudal swinging action to the left or right. Moreover, for particular problems of patients, the caudal flexion lock lever may be locked while manipulation is achieved only by caudal swinging and in converse, the caudal swing lock lever may be locked while caudal flexion or distraction is accomplished. Caudal manipulation may also be assisted by use of the detachable assist arm or handle 46 in order to improve the chiropractor's working position in an upward or downward direction applied outwardly of the ball joint 60 and 62. The detachable assist bar 46 also provides better leverage for the chiropractor to swing the caudal section in lateral caudal flexion.

In accordance with an important feature of the present invention, the caudal section 40 is provided with a unique leaf spring assembly 64 resisting the manipulation in caudal flexion distraction and for reducing the amount of vertically applied forces that are required of a chiropractor for caudal flexion in treating a patient on the table. The leaf spring assembly is generally designed so that a relatively constant amount of vertically applied external force is needed to move the caudal section throughout its range of vertical movement between upper and lower positions as shown in FIGS. 5A and 5B.

Figure 19:
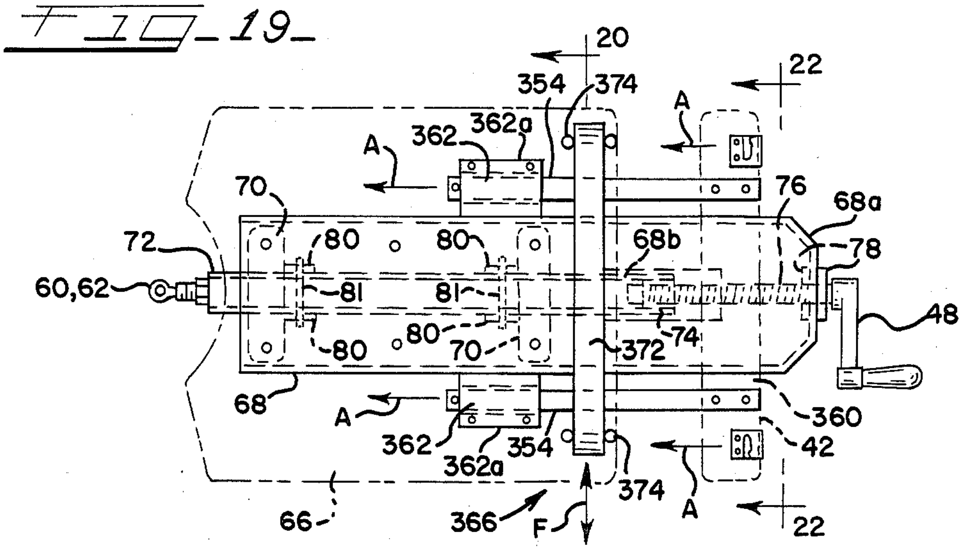
FIG. 19 is a top plan view of the caudal support section of the patient treatment table showing details of an ankle support and adjustment feature for accomodating patients of different height.
Figure 20:
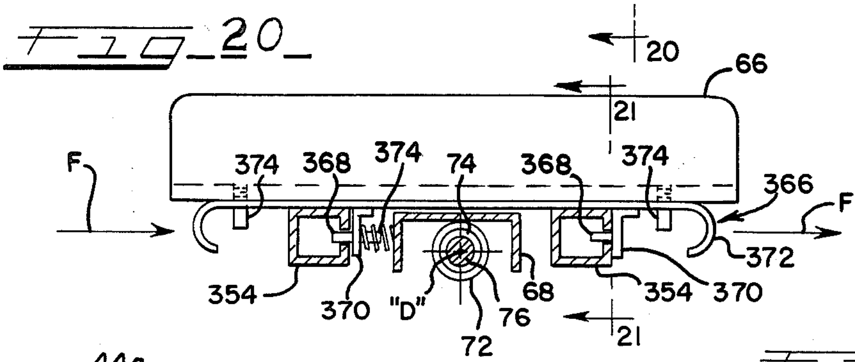
FIG. 20 is a transverse cross-sectional view taken substantially along lines 20—20 of FIG. 19.

Referring now more particularly, to FIGS. 5, 5A, 5B, 6 and 7, the caudal section 40 includes a generally flat lower torso support cushion 66 attached to the upper web of a centrally disposed, longitudinally extending, metal base 68 of channel-shaped transverse cross section. The channel-shaped base is provided with an outer end wall 68*a* adjacent the rear caudal crank 48 (FIG. 19) and the channel base and cushion 66 are supported for relative rotational movement about the axis D—D by a pair of pillow block bearings 70 secured to the upper web of the base with appropriate fasteners and journalled for rotation on an elongated, hollow tubular support member 72 of circular transverse cross section. An inner end of the tube is connected to the upper ball joint 60 and an outer e d of the tube projects outwardly beyond the leg support cushion 66 and is provided with a hollow, internally threaded insert 74 for threadedly receiving the inner end portion of a threaded jack screw 76 (FIG. 19). The jack screw extends outwardly through an aperture in the end wall 68*a* of the channel base and the rear caudal crank 48 is mounted on the outer end portion for rotating the jack screw. A spherical self aligning bearing 78 is keyed to an outer end portion of the jack screw to prevent longitudinal translation of the jack screw relative to the end wall 68*a* of the base. Accordingly, when the rear caudal crank 48 is turned, the channel base 68 and the caudal support cushion 66 are movable toward and away from the ball joint 60 to adjust support for patients of different height.

The leaf spring assembly 64 is supported from the hollow tubular column 72 by means of pairs of upstanding lugs 80 which project upwardly from the upper web surface 82*a* of a lower, elongated channel base 82 having downturned side flanges 82*b* along opposite edges of the web. Attachment bolts 81 are provided to secure the respective pairs of lugs 80 to the hollow longitudinal support tube 72 at spaced apart positions adjacent opposite end portions of the tube.

Each downwardly extending side flange 82*b* of the channel base 82 is provided with a pair of downwardly depending lugs 84 and 86 secured to the flange by welding or appropriate fasteners and spaced longitudinally apart as illustrated best in FIG. 5. The lugs 84 provide support for a pair of T-shaped link members 88 of a linkage assembly 90 provided for interconnecting the leaf spring assembly 64 and the lower ball joint 62. An upper end portion of each T-link 88 is pivotally connected to one of the respective lugs 84 by a pivot pin on bolt 92 and lower end portions of the T-links are pivotally interconnected to an axle pin 94. The axle 94 is journalled in a transverse sleeve 96 extending between the T-links and joined to the outer end portion of a thrust link 98 of adjustable length having an inner end portion secured to tne lower ball joint 62.

when the caudal support section is manipulated during flexion distraction movement from an upper position (FIG. 5A) downwardly toward a lower position (FIG. 5B) the sleeve 96 on the outer end of the thrust link 98 is confined to an arcuate path as represented by the arcuate line 100 in FIG. 5. At the same time, the upper pivots 92 of the T-links 88 are confined to move on an arcuate path represented by the line 102. This action results in the T-links 88 pivoting in a counter clockwise direction from the position of FIG. 5A toward the position of FIG. 5B as downward pivoting support of the cushion 66 occurs.

Each T-link 88 is provided with a short leg 88*a* intermediate the upper and lower ends extending inwardly towards the vertical yaw axis extending between the upper and lower ball joints 60 and 62. The short legs 88*a* are interconnected by a transverse pivot axle 104 which is connected at right angles to the outer end of a guide rod 106 spaced above the thrust link 98 and mounted for longitudinal sliding movement in guide sleeve 108. The guide sleeve is connected to a transverse, hollow sleeve 110 at the inner end which is mounted on an axle pin 112 extending between a pair of spaced apart lugs 114 projecting outwardly of a hollow sleeve 116 mounted for rotation on a vertical pivot axle 118 which supports the upper and lower ball joints 60 and 62 at opposite ends. As illustrated in FIGS. 5, 5A and 5B, the rod 106 is longitudinally slidable in the sleeve 108 and the sleeve is rockable about the axle pin 112 as the caudal section is manipulated in flexion distraction movement.

The upper and lower ball joints 60 and 62 are supported at the ends of the axle pin 118 which in turn is supported by a pair of fixed brackets 120 extending outwardly from the base structure 34 toward the caudal support section 40. The axle 118 is in general alignment with the caudal swing or yaw axis and as caudal flexion takes place from side to side, the sleeve 116 is rotatable on the axle because of the connection via the rod 106, sleeve 108 and axle 104 extending between the short legs 88*a* of the T-links 88.

The axle 104 which extends through the legs 88 of the links 88 is interconnected by a pair of shackle links 120 projecting upwardly and pivotally connected adjacent the upper ends to a pin 122 journalled in a hollow sleeve 124 secured to the outer end of a spring bracket 126. The spring bracket 126 is secured adjacent the outer end of an upper leaf of an elongated leaf spring 130 of the leaf spring assembly 64 and is alinged with and positioned below the channel base 82 between the side flanges 82*b* thereof. The spring bracket is attached to the upper leaf of the spring by a plate 128 and cap screws 129 so that the hollow sleeve 124 and axle pin 122 move with the outer end of the leaf spring as the spring is deflected during caudal flexion distraction manipulation.

As the caudal support section 40 is manipulated in caudal flexion distraction action between an upper position of FIG. 5A downwardly through the level position of FIG. 5 toward a lower position of FIG. 5B, the free outer end of the spring 130 is constrained by the linkage assembly 90 to move along a path indicated in FIG. 5 generally by the line 132. As downward deflection of the caudal support section 40 occurs, the spring offers distraction resistance against the deflection. The force provided by the spring 130 acts through an effective moment arm measured between the axle pin 122 and the pivot pins 92 and this moment arm decreases in length as deflection increases so that the amount of external force required to deflect the caudal section is maintained at a substantially constant value regardless of the amount of angular deflection downwardly from an upper, rest position of the caudal section as illustrated in FIG. 5A.

Figure 7:
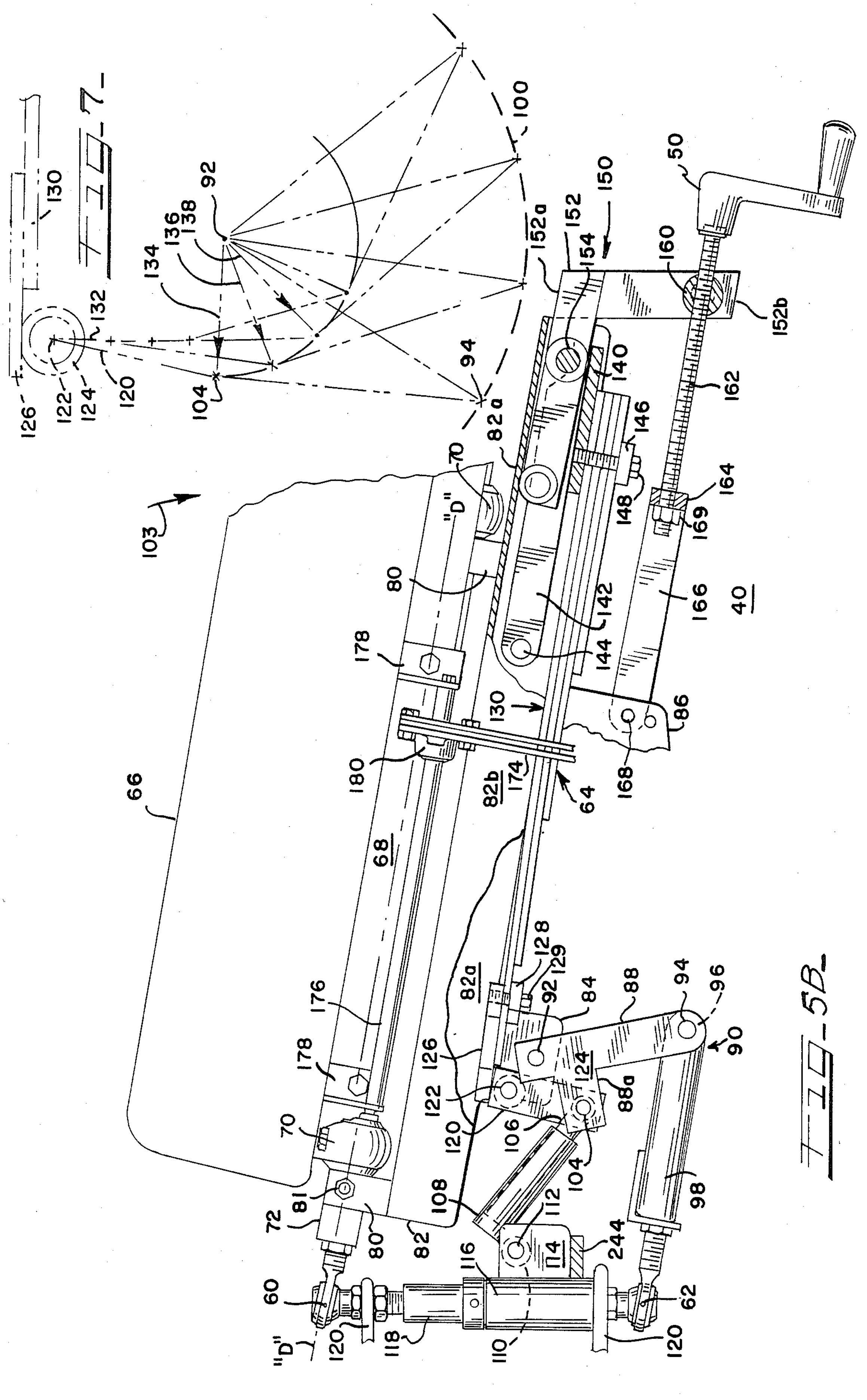
FIG. 7 is a diagrammatic and schematic view of the paths of the several pivot points of the linkage mechanism for interconnecting the leaf spring assembly and the ball joints supporting the caudal support structure from the base of the table.

Referring to FIG. 7, the graphical illustration therein represents the pivot pin 92 as being fixed relative to movement of the axle 94 along the arc 100 and the moment spring pin 122 along a path 132. The decreasing effective moment arm values as downward deflection occurs, are represented by the arrows 134, 136 and 138 which arrows extend from the fixed pivot 92 outwardly as shown and graphically illustrate the decreasing effective moment arm which is provided by the linkage assembly 90 acting on the outer end of the leaf spring 130. This arrangement results in a substantially uniform force being required to manipulate the caudal support section 40 in flexion distraction regardless of the amount of angular deflection of the caudal support cushion 66 relative to the level position as shown in FIG. 5 thereof.

In an embodiment constructed in accordance with the present invention, an upward external pulling force is required to deflect the caudal support section upwardly from the level position of FIG. 5 to an upper position (arrow 101) of FIG. 5A and this force is substantially the same over a range of angular slopes ranging from zero or level to a upward angle of a maximum of plus 10°. The amount of external downward force to pivot the caudal section from the level position of FIG. 5 to a downward sloping position (arrow 103) of FIG. 5B up to a maximum of 20° downwardly is equal to the upward pull and generally independent of the amount of angular deflection up or down. In accordance with spring laws, the amount of force required to deflect a spring is generally proportional to the amount of deflection and the unique linkage assembly 90 of the present invention provides a change in moment arm so the forces (arrows 101 and 103) required for upward and downward spring deflection are substantially constant and independent of the amount of spring deflection away from the level position either upwardly or downwardly.

The elongated leaf spring 130 includes a plurality of individual spring leaves which diminish in length starting from an uppermost longest leaf as shown. The multiple leaves of the spring are secured together adjacent an outer end of the spring assembly against a support plate 140 extending transversely between a pair of pivot legs 142 secured to the channel 82 for pivotal movement about inner end portions of the legs on a pivot axle 144. The leaves of the spring assembly are clamped against the base plate 140 by means of a clamping bar 146 and cap screws 148 so that the outer end portion of the leaf spring 130 is pivotally secured to the channel base 82 between the depending flanges 82*b* thereof for movement around a transverse pivot axis spaced between the opposite ends of the spring.

In accordance with an important feature of the present invention, the table 30 is provided with a spring tension adjustment assembly 150 controllable by the adjustment crank 50 to provide selectively variable amounts of pre-stress upon the leaf spring 130 for leveling the cushion 66 when patients of different weight are treated. Adjustment of the prestress on the spring 130 by the crank is initiated when a patient first lays on the table prior to treatment and thereafter automatic leveling of the caudal support section 40 in general alignment with the thoracic support section 36 takes place when external manipulation forces are withdrawn.

The spring tension adjustment assembly 150 includes a pair of parallel L-shaped lever arms 152 having upper segments 152*a* spaced apart and supported on a transverse axle pin 154 which is detachably mounted to rest in semi-circular grooves provided on the upper edges and adjacent the outer ends of the legs 142. Inwardly end portions of the upper segments 152*a* are interconnected by an axle pin 156 (FIG. 5) parallel of the support pin 154 and a roller 158 is mounted on the pin for direct engagement against the underside of the web 82*a* of the channel base 82. The L-shaped arms 152 include downwardly depending legs 152*b* which are interconnected adjacent lower end portions by a transversely extending traveler bar 160 having a bore at the center for accommodating an elongated, threaded jack screw 162 which is turned by the adjustment crank 50 secured to the outer end of the jack screw.

An inner end portion of the jack screw extends through a smooth aperture provided in a cross member 164 which includes a transverse threaded nut 169 joined to the outer end of a pair of legs 166 which are pivotally connected to the lugs 86 by pivot pins 168. In order to pretension or prestress the leaf spring 130 to accommodate the weight of a particular patient resting on the table so that the caudal support section 40 will level automatically with respect to the caudal section 36, the crank handle 50 is rotated in either direction and the traveler pin 160 moves longitudinally of the jack screw to pivot the lower end of the legs 152*b* of the L-shaped members 152 about the axis of the pin 156. As illustrated in FIG. 6, clockwise movement of the L-shaped members 152 about the pin 156 results in clockwise movement of the spring support legs 142 about the axis of the pin 144 as the pin 154 moves the outer ends of the legs 142 downwardly. Accordingly, the outer end portion of the spring 130 is moved downwardly away from the web 82*a* of the channel base and because the opposite end of the spring is connected to the ball joint 62 through the linkage assembly 90 such downward movement of the outer end of the leaf spring results in bending stress being applied to the spring 130 as illustrated. A greater amount of bending of the spring is required to accommodate a patient of heavier weight resting on the table and a lesser amount of bending pre-tension may accommodate a patient of normal weight. Pretensioning of the spring in the manner described does not greatly affect the amount of external forces (arrows 101 and 103) that must be applied in manipulating the caudal section 40 in flexion distraction so that a similar feel to the chiropractor is provided regardless of whether the patient is relatively heavy or relatively light in weight.

Because the pin 154 rests in the upwardly open semi-circular grooves provided adjacent the outer end portion of the legs 142, the entire spring tension adjustment assembly 150 can be detached for service by outward withdrawal after a wedge block is inserted between the channel web 82 and legs 142 and after the tensioning stop nut 169 on the jack screw 162 is removed. This feature is also useful during initial assembly of the leaf spring assembly 64 and the linkage assembly 90 on the caudal support section 40.

In accordance with a feature of the present invention, the leg support cushion 66 of the caudal section 40 is adjustably rotatable about the axis D—D coextensive with the longitudinal axis of the hollow support tube 72. Referring to FIGS. 4, 5, 13 and 14, a caudal rotation lock system 170 controlled by the handles 52 on opposite sides of the table may be unlocked to permit a particular rotational position between the angular limits shown in FIG. 4 may be selected and the lock activated to maintain the cushion in a selected rotational position. The caudal rotation lock system includes an over-center toggle lock 172 shown in detail in FIGS. 13 and 14 mounted on one of the lugs 86 depending from the chassis base 82 for controlled, selectable locking and releasable engagement with a downwardly depending tang 174 (FIGS. 4 and 5) comprising a pair of thin, flat tang plates 174*a* spaced apart by a short, H-shaped spacer 174*b* sandwiched therebetween. At the upper end, the tang is journalled on an offset elongated rod 176 extending longitudinally parallel of the axis D—D on one side of the channel base 68. The rod is supported at opposite ends by a pair of clips 178 attached to one of the depending side flanges of the channel member 68. An upper end portion of the tang 174 is pivotally connected to the rod by a bearing assembly 180 which permits pivotal movement of the depending tang 174 relative to the longitudinal axis of the rod 176 and sliding movement along the rod 176 during adjustment of the position of the cushion 66 by the rear caudal crank 48 as previously described for accommodating patients of differing heights. After the caudal rotation lock 172 is released by downward pivotal movement of the control handle 52 as indicated by the arrow B, caudal rotation can be effected and if a selected angular rotational position is to be maintained during treatment, either lock handle 52 may be pivoted upwardly to activate the lock 172 to clamp the tang 174 and prevent further caudal rotation until the clamp is unlocked.

Figure 13:
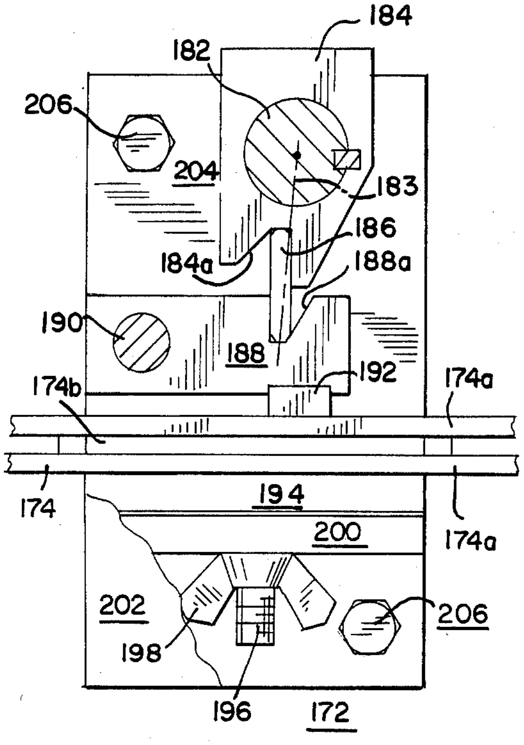
FIG. 13 is a side elevational view of another modified locking mechanism constructed in accordance with the features of the present invention and shown in a locked position.
Figure 14:
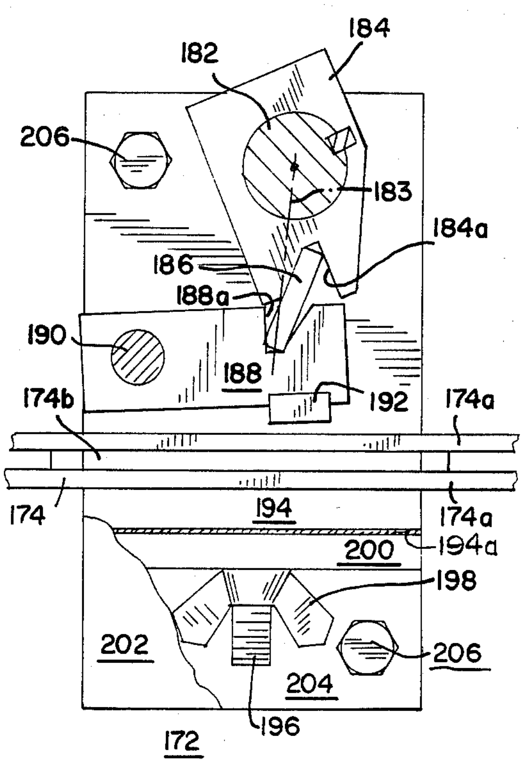
FIG. 14 is a view similar to FIG. 13 illustrating the locking mechanism in an unlocked position.

Referring to FIGS. 13 and 14, the caudal lock 172 is actuated by a shaft 182 extending transversely between opposite sides of the table and rotated by a handle or arm 52 on either side of the table as previously described. A lock lever 184 is keyed to rotate with the shaft and the lever is formed with a V-shaped groove 184*a* in one end thereof facing the tang 174 in order to accommodate a short rectangular, toggle link 186 which is pivotally movable past an over-center axis, to contact opposite divergent faces of the V-groove 184*a* when the lever is rotated from the locking position (FIG. 13) to the unlocking position (FIG. 14) in a counter clockwise direction as illustrated. An opposite edge portion of the toggle link 186 projects into a similarly shaped V-groove 188*a* formed in an opposing face of a pivoting jaw member 188 mounted for pivotal movement on a pivot shaft 190. An opposite face of the jaw member 188 is provided with a slot for receiving a replaceable clamping block or shoe 192 formed of relatively hard plastic material such as urathane or dense elastomer for clamping engagement against the adjacent face of the tang 174. Clockwise rotation of the lever 184 from the unlocked position (FIG. 14) toward the clamping or locking position (FIG. 13) causes the toggle link 186 to rotate and move across an over-center axis 183 extending between the central axes of the shaft 184 and the bottom of the V-groove 188*a* to exert thrust against the pivotal jaw member 188 to bias the jaw block 192 tightly against the surface of the tang 174 and prevent longitudinal displacement thereof. A fixed jaw 194 is disposed for engagement with an opposite face of the tang assembly and the fixed jaw 194 is secured by a threaded stud 196 and wing nut 198 to a wall member 200 sandwiched between a pair of parallel side plates 202 and 204 forming the body of the lock 172, which body is secured to the depending lug 86 on the channel base 68 by fasteners such as cap screws 206. A shim 194*a* may be inserted to increase locking force.

The divergent surfaces of the respective V-grooves 184*a* and 188*a* provide limiting stop surfaces controlling the range of angular disposition of the toggle link 186 as the link pivots across the overcenter axis 183 between locking and unlocking positions. Engagement between the toggle link 186 and one surface of each groove 184*a* and 188*a* also limits the amount of travel of the lever 52 to approximately 30° between the locked and unlocked positions. The over-center toggle lock 172 provides a bistable lock system wherein the lock remains in the last position (locked or unlocked) as selected by the lever 52 until the next movement of the lever takes place.

Referring now to FIGS. 1, 5, 11 and 12, the table 30 includes a caudal flexion distraction lock assembly 210 controlled by the levers 54 on opposite sides of the table as illustrated. The lock assembly 210 includes a lock 212 generally similar to the lock 172 and adapted for locking and releasing engagement with a tang 214 which is pivotally interconnected at an inner end to the lower axle pin 94 extending between the lower ends of the T links 88 of the linkage mechanism 90. When the lock 212 is in a locked position with the levers 54 in the generally horizontal position as shown in FIG. 1, the tang 214 is clamped tightly by the lock and the link 98 can no longer pivot through a normal range of movement at the outer end as indicated by the arcuate path 100. The lock action prevents manipulation of the caudal section 40 in vertical flexion distraction. When the lock 212 is released permitting relative sliding movement of the tang 214 through the lock jaws, caudal flexion distraction in a vertical direction can be implemented freely.

Control of the lock 212 is achieved by a rotating shaft 214 extending between opposite sides of the table and supporting the operating handles 54 on opposite end portions thereof for easy actuation on either side of the table. The shaft 214 is keyed to rotate a lever 216 having a V-groove 216*a* with divergent faces for angle limiting engagement with a short, rectangular, toggle link 218 which is adapted move over-center across the plane 217 as the lever is pivoted in a counter clockwise direction from the locking position of FIG. 11 to an unlocked position of FIG. 12.

Figure 11:
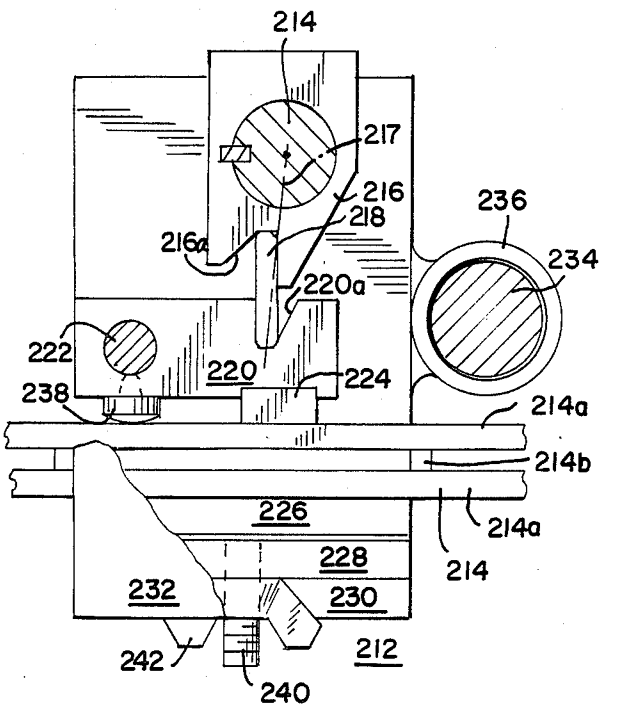
FIG. 11 is a side elevational view with portions broken away and in section of a modified locking clamp assembly constructed in accordance with the features of the present invention and shown in a locking position.

The lock includes a pivoting jaw 220 having a V-groove 220*a* facing the V-groove 216*a* for receiving a portion of the toggle link 218 which is rotatably movable relative thereto in a manner as described previously in connection with the lock 172. The pivoting jaw 220 is mounted for pivotal movement on a pin 222 and includes a recess on an opposite face from the V-groove 220*a* for holding a jaw block or shoe 224 of relatively rigid and stiff urathane material or dense elastomer adapted to engage the adjacent surface of a tang member 214*a* for clamping engagement as shown in FIG. 11. On an opposite side of the tang 214, a fixed jaw 226 is in contact and supported by a transverse wall 228 extending between opposite side plates 230 and 232 comprising a body of the lock 212. The jaw 226 is attached to the wall 228 with a threaded stud 240 and wing nut 242 for easy replacement when required. A shim 226*a* may be added to increase locking force.

Figure 12:
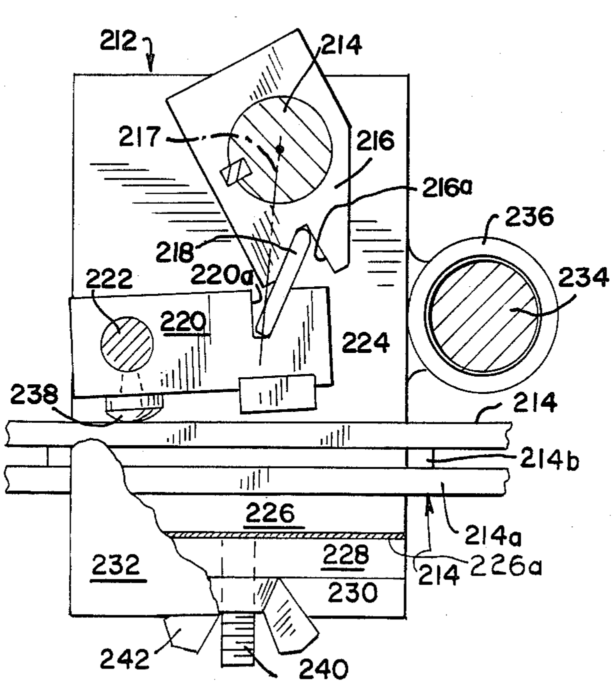
FIG. 12 is a view similar to FIG. 11 illustrating the locking mechanism in an unlocked position.

The body of the locking mechanism is supported for pivotal movement (arrows 235) between the lugs 86 on the base 82 on a pivot pin or bolt 234 which projects through a hollow circular sleeve 236 welded to the side plates 230 and 232 as shown in FIGS. 11 and 12. Because the body is pivotal about the support pin 234 (arrow 235—FIG. 5), the pivotal jaw 220 is provided with a low friction, plastic button 238 adjacent the pin 222 for engagement with the adjacent surface of the tang 214 to limit pivotal movement of the lock body when the lock is unlocked as best illustrated in FIG. 12.

The respective lock units 172 and 212 have been found to provide long periods of service free operation with more than adequate clamping force and minimal wear on the respective jaw blocks 192, 224 and corresponding fixed jaw members 194 and 226. Wear and tear on the surfaces of the tangs 174 and 214 is minimized by the use of jaw blocks of plastic material and the unique bistable operation of the clamping locks which retain the jaws in an open position whenever the units are unlocked. When the levers 54 are pivoted downwardly to unlock the lock 212, the caudal support section 40 may be moved freely in flexion distraction manipulation between upper and lower positions as indicated by FIGS. 5, 5A and 5B, previously described. Should it be desired by a chiropractor to lock the caudal support section 40 against flexion distraction manipulation in a vertical direction so that lateral flexion could be provided without vertical movement, the locking levers 54 are pivoted upwardly to tightly clamp the lock unit 212 on the tang 214 and prevent flexion distraction manipulation as described.

In accordance with the previous description, the rod 106 slidable in the sleeve 108 and the transverse sleeve 112 attached thereto which is rotatable on the pin 110 provide a means for rotating the sleeve 116 on the pivot axle 118 between the ball joints 60 and 62 to follow lateral flexion of the caudal support section 40 as the section is manipulated about a vertical yaw axis relative to the thoracic support section 36. A transverse, outwardly extending lever arm 244 (FIG. 15) is pivotal around the vertical axis of the shaft 118 lateral as caudal flexion takes place as indicated by the arrow E. An outer end portion of the arm 244 is pivotally interconnected with a generally horizontally extending tang 246 mounted on one side of the base structure 34, as shown in FIG. 15. The tang 246 and the arm 244 are components of a lateral flexion lock system 250 controlled by the levers 58 on opposite sides of the table 30. The lateral flexion locking system includes a lock 252 substantially identical to the locking unit 172 as previously described and controlled by a rotating shaft 254 projecting outwardly from opposite sides of the base structure 34 having handles 56 on opposite ends for rotational control of the shaft to lock and unlock the lock 252 as desired to prevent or permit lateral flexion of the caudal support section 40 from side to side as previously described.

The pivotal, thoracic support section 36 of the table is provided with a thoracic support cushion 260 supported for rotation about a longitudinal pivot axis generally coincident with the spinal axis of a patient 32 supported on the table. In FIG. 2 this axis is designated by the letter C and is the axis spaced above the upper surface of the cushion 260 which is illustrated in a horizontal or neutral position in solids lines and in dotted lines in sloped positions right or left, tilting upwardly at angles of up to 25°. The thoracic cushion is supported on a pair of arcuately curved, depending support rods 262 extending transversely of the table and the rods are pivotally attached adjacent upper, opposite ends to brackets 264 attached to the underside of the base of the thoracic cushion 260. As illustrated in FIG. 2, the rods 262 are curved with a radius generated from the spinal axis C so as to provide the rotational flexion of the spine of the patient for derotation treatment in a precise angular degree and direction.

The transverse arcuate support rods are spaced apart longitudinally of the table and each is supported in a pair of self-aligning generally spherically shaped bearings 266 formed of relative rigid plastic material. The bearings are secured between pairs of bearing flanges 268 attached to opposite sidewalls 270 of the support base structure 34. The generally spherical bearing elements 266 are provided with a bore slightly oversize in comparison to the outer diameter of the curved support rods 262 in order to accommodate the curvature and still permit smooth and free longitudinal sliding movement of the rods in the bearing bores.

Rotational control of the thoracic support cushion 260 is further facilitated by a pair of depending handles 272 provided on opposite sides of the support cushion intermediate the ends of the thoracic support section between the curved support rods. The table 30 is provided with a pivotal thoracic control lock system generally indicated by the numeral 274 which is controlled by the levers 58 movable downwardly from the generally horizontal, locked position in the direction of the arrows B to unlock the pivotal thoracic section for pivotal movement of the thoracic cushion 260 relative to the spinal axis "C" of the patient (FIG. 2). Each control lever 58 is connected to the outer end of a common control shaft 276 extending between opposite sides of the table through openings provided in the base section sidewalls 270.

Referring to FIGS. 8, 9 and 10, the shaft 276 is rotatable by movement of the pivotal thoracic lock levers 58 to operate a thoracic lock unit 278 of the over-center, toggle locking type generally similar to the lock units 172, 212 and 252 as previously described. The thoracic lock unit includes a lever 280 keyed to rotate with the shaft and provided with a V groove **280*a* on an inner end thereof adapted to receive a short, rectangular toggle link 282 having an opposite edge engaged within a facing V-groove 284*a* of a pivotal jaw member 284 mounted on a pivot pin 286. The toggle lock element is pivoted to move across a center plane 281 to provide a bistable toggle locking feature as previously described. An opposite face of the pivoting jaw 284 is formed with a recess for receiving a jaw block 288 of rigid elastomer material adapted to engage the surface of a thin, flexible sheet of spring material 290 attached to an outer spring leg 292*a* of a Z-shaped spring jaw 292. When the shaft 276 controlled by the handles 58 is pivoted in a clockwise direction from the unlocked position of FIG. 10 to the over-center toggle locking position of FIG. 9, the Z-shaped spring jaw 292 is biased tightly against the adjacent surface of the curved, cushion support or trunion rod 262 connected to the thoracic cushion 260. The support rod is pressed tightly and clamped against a fixed jaw block or mounting plate 294 and is restricted from longitudinal displacement once the lock is moved to the locked position by operation of the pivotal thoracic lock lever 58. When the control shaft 276 is rotated in a counter clockwise direction from the position of FIG. 9 toward the unlocked position of FIG. 10, the Z-shaped spring jaw 292 deflects the jaw lever 284 to pivot in a counter clockwise direction about the pin 286 and the outer spring leg 292*a* moves away from contact with the curved trunion support rod 262 so that the rod may then move freely in a longitudinal direction in the bases of the self-adjusting spherical bearings 266 to any desired position of thoracic pivotal rotation as selected (FIG. 4**).

The locking unit 278 includes a pair of side plates 296 extending outwardly from the rectangular mounting jaw plate 294 and the control shaft 276 is supported for rotation by the spaced apart side plates as shown best in FIG. 8. Each side plate 296 is provided with an enlarged slot adjacent the jaw plate 294 to accommodate movements of the arcuately curved support rod 262. A lock unit 278 is mounted in position on a wall 298 extending transversely between the sidewalls 270 of the base structure 34 as shown in FIG. 2 and is secured in a position thereon by a pair of fasteners 299, a lower one of which passes through an inner leg **292*b* of the spring jaw member 292** to secure the spring jaw in place.

All of the four over-center toggle locking units, 172, 212, 252 and 278 operate in generally the same fashion and provide long and useful carefree service with excellent holding characteristics and minimal force being required of a chiropractor for locking or unlocking the clamping engagement thereof. In addition, all of the control levers 52, 54, 56 and 58 are duplicated on each side of the table and the locks are arranged so that the levers are generally horizontal in a locked position and are unlocked by downward pivotal movement as indicated by arrows B in FIGS. 1 and 5.

Referring now to FIGS. 1 and 3, the head section 38 is supported from the sidewalls 270 of the support base structure 34 and includes a pair of longitudinally extending, elongated head supporting cushions 300 which are spaced apart and parallel to permit the patient to lay face down in comfort as shown in FIG. 3. The head cushions are interconnected and supported on a U-shaped, transversely extending bracket 302 mounted to surface 310. Fasteners such as bolts 304 are utilized to secure the transverse bracket 302 to surface 310 and the head supporting cushions 300 in place. At a lower level, the head section 38 is provided with a pair of arm supporting cushions 306 extending longitudinally of the table and spaced downwardly and outwardly of the head supporting cushions 300. The elongated arm supporting cushions are supported on cross members 308 attached to the bottom surface 302 of the base structure 34 by appropriate fasteners 312 as shown in FIG. 3. A roll of sanitized paper 314 is provided to overlay the upper surface of the head supporting cushions 300 and a knife edge cutting attachment 316 is provided along the side of one head cushion to facilitate cutting or tearing off of a section of the paper after usage.

In accordance with the present invention, the base support section 34 is provided with an upstanding column portion 318 of generally hollow rectangular tubular cross section joined at its front edge to a cross member 270*a* between sidewalls 270 of the base by bolts or suitable fasteners 270*b*. The column or pedestal 318 is provided with a bottom wall 320 having a plurality of threaded apertures therein for receiving elongated cap screws or bolts 322 projecting upwardly for attaching an enlarged, channel-shaped, horizontal base 324 extending longitudinally outwardly of the pedestal column 318 in opposite directions as shown in FIG. 1. The channel base 324 has a planar upper web 324*a* and a pair of downwardly depending, longitudinally extending opposite side flanges 324*b* which are spaced laterally outwardly of the upstanding pedestal column 318 as shown in FIG. 2. In order to provide increased lateral stability for the base structure 34 and the table 30 as a whole, there are provided a pair of floor surface engaging, transverse feet 326 having beveled outer edges and secured to bosses 324*c* provided at opposite ends of the elongated channel 324. The lateral feet 326 are relatively thin and the upwardly and inwardly sloping beveled edges to further stabilize the table in a lateral direction. Upwardly extending detachable fasteners 330 are threaded into bosses 324*c* provided on the underside the base channel 324 to secure the thin, flat feet 326 in place. It should be noted from FIG. 1 that the base channel 324 extends longitudinally of the table in opposite directions for a substantial distance from the upstanding pedestal section 318. This extension provides excellent stability for the table 30 while the caudal manipulation of a patient is taking place and especially with respect to a lateral pitch axis extending across the pelvic or hip region of the patient. Moreover, the relatively narrow base channel 324 permits the chiropractor to walk relatively close to the central axis of the table without impediment.

In accordance with an important feature of the present invention, the height or working level of the upper surface of the respective patient support sections may be adjustably controlled by the inclusion of one or more hollow tubular pedestal spacer sections 332 interposed between the upper web 324*a* of the base channel 324 and the lower end wall 320 of the pedestal column 318. Spacer segments may be stacked one upon the other to provide a wide variety of table working levels between 20" and 32" and the bolts 322 are of correspondingly different lengths in order to accommodate the number and size of spacers that are used in a particular application.

When relatively heavy or tall patients are treated, it is desirable to provide the chiropractor with an increased convenience for moving the caudal support section 40 in flexion distraction movement in a vertical direction as well as in caudal swing flexion from side to side as previously described. To assist manipulation, an assist bar 46 may be detachably mounted on the channel base member 68 of the caudal section 40 within an elongated slot 68*b* provided in the upper flange of the channel base for this purpose. The assist bar 46 includes an upstanding hollow column 334 with a control knob 336 at the upper end and a flat rectangular or square shaped base plate 338 attached to the lower end of the column and dimensioned to span across the transverse width of the slot 68*b*. Intermediate the ends of the assist bar column 34 a branch socket 340 is attached slope upwardly and outwardly thereof at approximately a 45° angle for supporting a hollow arm 342 having a transverse tubular handle 344 at the upper end for providing a convenient means for grasping the assist bar 46 facilitating the manipulation of the caudal support section 40 as desired. Normally, the detachable assist bar is positioned between the legs of the patient with the underside of the rectangular base plate 338 resting on the upper surface of the channel base 68 and centered along the longitudinal axis C—C bisecting the elongated slot 68*b*.

The rotatable handle 336 at the upper end of the column 334 is connected to a threaded rod 346 extending downwardly along the column center through an opening in the base plate 338 to support a rectangular lock plate 348 attached at the lower end of the rod. The lock plate has an upper surface spaced below the lower surface of the base plate 338 by a distance slightly greater than the thickness of the web of the channel base 68. To facilitate positioning of the assist bar in relation to the elongated slot 68*b*, a pair of relatively short pins 350 are provided on the plate 338 at diagonally opposite locations to extend downwardly from the underside of the base plate into the slot between the opposite edges.

A pair of relatively long pins 352 are provided at opposite corner portions as best shown in FIG. 18 so that when the lock plate 348 is rotated 90° it is movable between a locking position shown in solid lines (FIG. 18) wherein a longer axis of the locking plate is transversely positioned relative to the axis C—C and a non-locking position shown in dotted lines wherein the longer axis of the locking plate 348 is aligned parallel of the axis C—C centered between the opposite sides edges of the slot 68*b*. The long pins 352 serve as stops for limiting rotational movement of the locking plate beyond 90° between the locking and unlocking position as illustrated and described and when it is desired to detach the assist bar 46, the handle 336 is turned to rotate the locking plate from the transverse position (FIG. 18 solid lines) to the release position (dotted lines) so that the assist arm can then be withdrawn upwardly from the base 68. Because the slot 68*b* in the upper web of the base is substantially longer than the dimension of the locking plate 348, the assist bar 46 may be attached at a variety of different longitudinal positions along the length of the slot outwardly from the universal joints 60 and 62. The position of attachment is chosen so as to facilitate caudal flexion distraction and caudal swing flexion in a lateral direction as needed.

Figure 21:
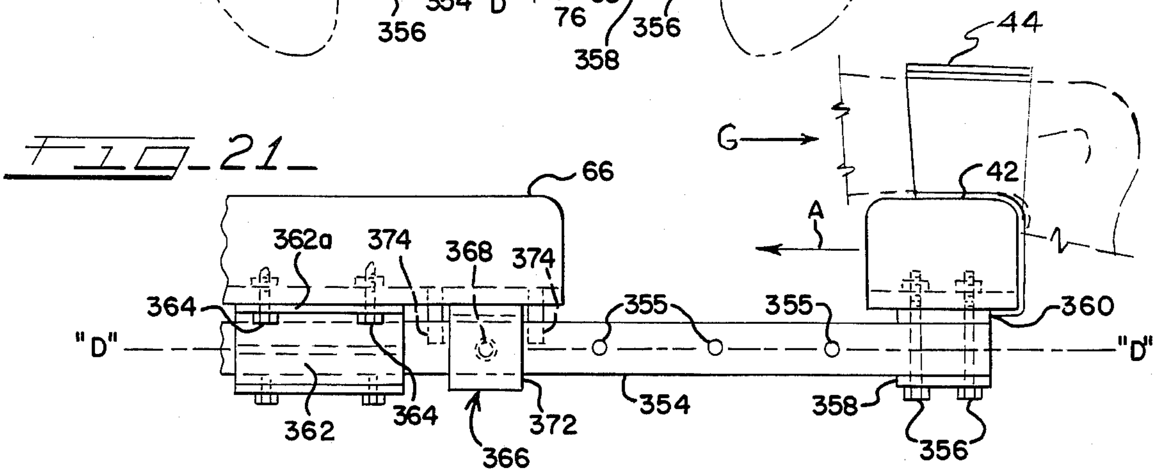
FIG. 21 is a fragmentary cross-sectional view taken substantially along lines 21—21 of FIG. 20.

The ankle support cushion 42 is adjustable longitudinally in discrete intervals relative to the outer end of the caudal cushion 66 to accommodate patients of different heights. Referring to FIGS. 15 and 19 through 22, there is provided an adjustable support system comprising a pair of elongated hollow tubular legs 354 disposed in parallel on opposite sides of the base channel 68 for supporting the ankle cushion at the outer end of the legs. The tubular legs are preferably of square or rectangular transverse cross section and are attached to the ankle cushion 42 by means of fasteners 356 projecting upwardly through drilled apertures in shim plates 358. The fasteners extend up through the upper and lower walls of the legs and 354 through openings in a cross plate 360 underlying a base board of the ankle cushion. T-nuts or other threaded fasteners are provided on the upper surface of the base board as shown in FIGS. 21 and 22 to receive the threaded upper end portions of the fastening bolts 356.

Inner end portions of the elongated hollow legs 354 are supported for sliding adjustment from the underside of a base board of the caudal cushion 66 by guide sleeves 362 of rectangular cross-section. As previously indicated, the ankle rest cushion 42 is movable inwardly and outwardly with respect to the outer end of the main caudal cushion 66 and an ankle rest locking assembly generally indicated by the reference numeral 366 is provided for securing the ankle rest in a selected position relative to the main caudal cushion. The hollow support tubes 354 are formed with apertures 355 in the sidewalls thereof at spaced longitudinal intervals in order to receive locking pins 368 provided on downwardly extending brackets 370 (FIG. 20) mounted on the underside of an actuating bar 372 having curved opposite end portions. Longitudinal movement of the bar in the direction of an arrow F is effective to move the pins out of locking engagement in a pair of aligned apertures 355 in the sidewalls of the spaced apart elongated tubular legs 354. A bias spring 374 is mounted on one of the lock pins 368 biases the locking bar outwardly from adjacent flange of the channel base 68 toward the locking position. When manual force is applied in direction of the arrows F, FIG. 2, the pins 368 are moved out of the apertures 355 so that the ankle rest cushion 42 may be manually moved inwardly or outwardly with respect to the main caudal cushion 66 until a discrete position is selected. Upon release of pressure on the bar 372, the pins then become reengaged or locked within the adjacent apertures 355. It will thus be seen that the ankle rest 42 is movable between selected intervals of spacing outwardly from the end of the main caudal cushion 66 and is then lockable in a selected position with the pins 368 engaged in the apertures 355 of the legs 354.

The locking bar 372 is supported for transverse movement in the direction of arrows F and for reverse directional movement on the main channel base 68 and the hollow tubular legs 354. The bar is positioned beneath the outer end portion of the base of the cushion 66 and is restricted against longitudinal displacement in the direction of the axis D—D by pairs of guide pins 374 depending downwardly from the cushion base on opposite side edges of the locking bar. As shown in FIG. 19, two pairs of guide pins 374 are provided adjacent opposite end portions of the locking bar 372.

In accordance with another feature of the present invention, the ankles of a patient are securely attached to the cushion 42 at spaced apart locations on the ankle rest by the ankle cuffs 44. The cuffs are attached by straps 376 connected to the underside of the ankle rest cushion by brackets 378 and fasteners 380. The ankle cuffs are adapted to tension the patient's legs along their axis without twisting or tensing of the patient's limbs. The cuffs are designed to exert a well centered outward pull on each ankle as indicated by the arrow G and thus do not impart twisting action to the limbs as do some ankle securing devices. Each ankle cuff is provided with a detachable fastening section 44*a* on opposite side stacks such as a patch of "Velcro" tape in order to accommodate different sizes of a patient's ankle and to permit easy and rapid attachment and detachment as desired. Preferably the fasteners are of a Velcro type, commonly availble for strap bindings and the like.

From the foregoing, it will be seen that the new and improved flexion distraction table 30 provides a number of important features which aid the chiropractor in manipulating a patient during treatment. The pivotal thoracic support section 36 permits derotation treatment and the caudal support section 40 permits caudal flexion distraction as well as caudal lateral swing manipulation and the caudal cushion 66 is also to provide caudal rotation.

An important feature of the table is the use of new and unique lock mechanisms and control levers duplicated on opposite sides of the table permitting a chiropractor to operate from either side and eliminating the need for walking around the end of the table. In addition, the new and unique ankle support and cuff system provides for good security so that a patient is not likely to roll off of the table during treatment. An important advance in the table 30 is the leaf spring assist assembly 64, linkage assembly 90 and the spring tension adjustment assembly 150 for maintaining a substantially constant level of external force required for caudal flexion distraction during manipulation and for providing leveling action for patients of different weight.

The table 30 is extremely stable in both a lateral and longitudinal direction and affords the chiropractor a convenient means of providing increased stability with the unique base design. The detachable assist bar 46 also comprises an important feature which reduces chiropractor fatigue and permits heavy patients to be manipulated with relative ease in generally the same manner as a much lighter patient.

Although the present invention has been described with reference to a single illustrated embodiment thereof, it should be understood that numerous other modifications and embodiments can be made by those skilled in the art that will fall within the spirit and scope of the principles of this invention.

What is claimed as new and is desired to be secured by Letters Patent is:

1. A chiropractic table for supporting a patient, comprising:

base means projecting upwardly of a floor to a convenient working level;

first cushion means of said base means for suporting the thorax of a patient lying on said table for treatment;

second cushion means on said base means adjacent said first cushion means for supporting the lower torso of the patient;

ball joint means interconnecting said second cushion means and said base means to permit pivotal movement of said second cushion means about a horizontal axis extending generally transversely of the spinal axis of said patient between an upper position and a lower position;

leaf spring means normally biasing said second cushion means toward said upper position; and control linkage means for automatically reducing the biasing force exerted by said leaf spring means as said second cushion means is moved toward said lower position whereby said second cushion means is manipulated by a chiropractor to pivot about said horizontal axis between said upper and lower positions by the application of a relatively uniform amount of vertical force applied thereto for flexion distraction of a patient lying on said table for treatment.

2. The table of claim 1, wherein; said second cushion means is biased by said leaf spring means to slope upwardly from said adjacent end of said first cushion means in the absence of a patient lying on said table and is movable through an intermediate position generally level with said first cushion means when provided toward said lower position.

3. The table of claim 2 which includes leaf spring adjustment means for selectively adjusting the biasing force with which said leaf spring biases said second cushion means toward said upper position.

4. The table of claim 3, wherein said leaf spring means extends longitudinally of said second cushion means and rearwardly of said ball joint means, and wherein said spring adjustment means acts to pretension said leaf spring means so as to compensate for variations in the weight of a patient lying on said table.

5. A table as set forth in claim 1, wherein said transversely extending axis is located between said first and second cushion means.

6. A table as set forth in claim 5, wherein said leaf spring means is positioned beneath said second cushion means and extends generally parallel thereto, one end of said leaf spring means being connected to said second cushion means and the other end thereof being connected to said control linkage means.

7. A table as set forth in claim 6, wherein said ball joint means includes an upper ball joint to which said second cushion means is connected and a lower ball joint in vertical alignment with said upper joint and connected to said control linkage.

8. A table as set forth in claim 7, wherein said control linkage includes a first link extending generally parallel to said second cushion means and having one end thereof connected to said lower joint, and a second link interconnecting the other end of said first link and said second cushion means, said other end of said leaf spring means exerting said biasing force on said second link, thereby normally to bias said second cushion means to said upper position.

9. A table as set forth in clim 8, wherein said control linkage includes a third link interconnecting said other end of said leaf spring means and a point on said second link which is offset from the axis thereof so that the moment arm of said leaf spring means acting through said third link into said second link is reduced as said second cushion means is moved toward said lower position.

10. A table as set forth in claim 5, wherein said ball joint means also permits movement of said second cushion means about a vertical axis which intersects said horizontal axis, and means for locking said second cushion means against rotation about said vertical axis.

11. A table as set forth in claim 10, wherein said ball joint means includes an upper ball joint to which said second cushion means is connected and a lower ball joint in vertical alignment with said upper joint and connected to said control linkage.

12. A table as set forth in claim 11, which includes a sleeve mounted on said base means for rotation about said vertical axis, and means interconnecting said sleeve and said control linkage so that rotation of said second cushion means about said vertical axis produces corresponding rotation of said sleeve about said vertical axis.

13. A table as set forth in claim 12, which includes an arm connected to said sleeve and extending transversely therefrom, a link pivotally connected to the outer end of said arm, and means for clamping said link to said base means, thereby to prevent said second cushion means from being rotated about said vertical axis.

14. A table as set forth in claim 13, wherein said clamping means includes a block mounted in said base means and having an opening therein through which said link extends, and means for holding said link in engagement with said block.

15. A table as set forth in claim 14 wherein said holding means comprises a pair of members pivotally mounted on said block and having cooperating recesses in the opposing faces thereof, and a toggle member positioned in said recesses and adapted upon rotation of one of said members to force the other member into engagement with said link and said link into engagement with said block.

16. A table as set forth in claim 15 which includes a shaft mounted on said block for rotation about a horizontal axis, said one member being connected to and rotatable with said shaft, and an arm connected to said shaft outside said block for rotating said shaft and said one member.

17. A table as set forth in claim 16 wherein said recesses are shaped to limit movement of said arm from a generally horizontal clamping position in which said other member holds said second link in engagement with said block to a lower released position in which said link is free to move within said opening in said block.

18. A table as set forth in claim 17 wherein said opposed recesses are generally V-shaped and said toggle member comprises a flat metal bar positioned edgewise in said V-shaped recesses.

19. A table as set forth in claim 18, wherein the sides of said V-shaped recesses cooperate with said metal bar to limit movement of said arm to movement between said generally horizontal position and said lower position.

20. A chiropractic treatment table for supporting a patient for manipulation which includes:

a support structure;

cushion means for supporting the legs of a patent lying on the table;

ball joint means interconnecting said cushion means and said support to permit pivotal movement of said cushion means about a horizontal axis extending transversely of the spinal column of the patient between an upper position and a lower position;

leaf spring means one end of which is mounted on said cushion means, said leaf spring means normally biasing said cushion means toward said upper position; and control linkage means for automatically reducing the biasing effect of said leaf spring means on said cushion means as said cushion means is manipulated by a chiropractor toward said lower position said linkage means including means for reducing the effective movement arm of said leaf spring means between said cushion means and said ball joint means to provide a relatively uniform amount of manipulation force required over an angular range of deflection of said cushion means between said upper and lower positions.

21. A table as set forth in claim 20, wherein said ball joint means includes an upper ball joint to which said cushion means is connected, and a lower ball joint in vertical alignment with said upper joint, said control linkage interconnecting the free end of said leaf spring means and said lower ball joint.

22. A table as set forth in claim 24, which includes a rod positioned beneath said cushion means and connected to said upper ball joint, and means for mounting said cushion means on said rod for rotation about the longitudinal axis of said rod.

23. A table as set forth in claim 22, which includes means for locking said cushion means in an adjusted position relative to said rod axis.

24. A table as set forth in claim 22, which includes a member mounted on said rod and movable therewith, said member being positioned beneath said cushion means, and means extending between said member and said cushion means for locking said cushion means in an adjusted position after it has been rotated about said rod axis.

25. A table as set forth in claim 24, wherein said locking means includes a link pivotally connected to said cushion means at a point spaced from said rod axis, and clamping means mounted on said member and in engagement with said link for clamping said link to said member after said cushion means has been rotated about said rod axis to a desired position.

26. A table as set forth in claim 25, wherein said clamping means includes a block mounted on said support member and having an opening through which said link extends, and means for holding said link in engagement with said block.

27. A table as set forth in claim 26, wherein said holding means comprises a pair of members pivotally mounted on said block and having cooperating recesses in the opposing faces thereof, and a toggle member positioned in said recesses and adapted upon rotation of one of said members to force the other member into engagement with said link and said link into engagement with said block.

28. A table as set forth in claim 27, which includes a shaft mounted on said block for rotation about a horizontal axis, said one member being connected to and rotatable with said shaft, and an arm connected to said shaft outside said block for rotating said shaft and said arm member.

29. A table as set forth in claim 28, wherein said recesses are shaped to limit movement of said arm from a generally horizontal clamping position in which said other member holds said link in engagement with said block to a lower released position in which said link is free to move within said opening in said block.

30. A table as set forth in claim 29, wherein said opposed recesses are generally V-shaped and said toggle member comprises a flat metal bar positioned edgewise in said V-shaped recesses.

31. A table as set forth in claim 30, wherein the sides of said V-shaped recesses cooperate with said metal bar to limit movement of said arm to movement between said generally horizontal position and said lower position.

32. A table as set forth in claim 21, which includes locking means connected between said control linkage and said cushion means for preventing said cushion means from being rotated about said horizontal axis.

33. A table as set forth in claim 32, wherein said control linkage includes a first link extending generally parallel to said cushion means and having one end thereof connected to said lower joint, and said locking means includes a second link pivotally connected to the other end of said first link, and means for clamping said second link to said cushion means to hold the same in a desired position about said horizontal axis.

34. A chiropractic table for supporting a patient which includes:

a support structure;

cushion means for supporting the legs of a patient lying on the table;

ball joint means interconnecting said cushion means and said support structure to permit pivotal movement of said cushion means about a horizontal axis extending transversely of the spinal column of the patient between an upper position and a lower position, said ball joint means including an upper ball joint to which said cushion means is connected, and a lower ball joint in vertical alignment with said upper joint;

leaf spring means, one end of which is mounted on said cushion means, said leaf spring means normally biasing said cushion means toward said upper position;

control linkage means for reducing the biasing effect of said leaf spring means on said cushion means as said cushion means is moved toward said lower position, said control linkage means interconnecting the free end of said leaf spring means and said lower ball joint and including a first link extending generally parallel to said cushion means and having one end thereof connected to said lower joint;

locking means connected between said control linkage means and said cushion means for prevention said cushion means from being rotated about said horizontal axis; said locking means including a second link pivotally connected to the other end of said first link;

means for clamping said second link to said cushion means to hold the same in a desired position about said horizontal axis;

said clamping means including a block pivotally mounted on said cushion means and having an opening therein through which said second link extends; and means for holding said second link in engagement with said block.

35. A table as set forth in claim 34, wherein said holding means comprises a pair of members pivotally mounted on said block and having cooperating recesses in the opposing faces thereof, and a toggle member positioned in said recesses and adapted upon rotation of one of said members to force the other member into engagement with said second link and said second link into engagement with said block.

36. A table as set forth in claim 35, which includes a shaft mounted on said block for rotation about a horizontal axis, said one member being connected to and rotatable with said shaft, and an arm connected to said shaft outside said block for rotating said shaft and said one member.

37. A table as set forth in claim 36, wherein said recesses are shaped to limit movement of said arm from a generally horizontal clamping position in which said other member holds said second link in engagement with said block to a lower released position in which said second link is free to move within said opening in said block.

38. A table as set forth in claim 37, wherein said opposed recesses are generally V-shaped and said toggle member comprises a flat metal bar positioned edgewise in said V-shaped recesses.

39. A table as set forth in claim 38, wherein the sides of said V-shaped recesses cooperate with said metal bar to limit movement of said arm to movement between said generally horizontal position and said lower position.

40. A table as set forth in claim 20, which includes means for preventing said cushion means from rotating about said horizontal axis.

41. The table of claim 20, which includes an assist bar secured to said cushion means and extending upwardly therefrom for facilitating movement of said cushion means about said horizontal axis by an operator.

42. The table of claim 41, wherein said assist bar is detachably secured to said cushion means.

43. The table of claim 41, wherein said assist bar is positioned to extend upwardly between the legs of a patient lying on said cushion means.

44. The table of claim 41, wherein said cushion means includes a support having a slot therein, said assist bar including a base portion adapted to be slidably positioned in said slot, and means for clamping said assist bar to said support at a desired position within said slot.

45. A chiropractic table for supporting a patient, comprising:

base means projecting upwardly of a floor to a convenient working level;

first cushion means on said base for supporting the thorax of a patient lying on said table for treatment;

second cushion means for supporting the lower torso of said patient during controlled spinal flexion;

ball joint means supportively interconnecting said second cushion means and said base means permitting pivotal movement of said second cushion means about a lateral axis generally transversely of the spinal axis of said patient between an upper position and a lower position sloping downwardly from an adjacent end of said first cushion means;

leaf spring means for normally biasing said second cushion means toward said upper position; and control linkage means for automatically modifying the biasing force exerted by said leaf spring means so that a substantially constant value of external force applied to said second cushion means is effective to pivot said second cushion means through a range of angular positions between said upper and lower positions.

46. The table of claim 45, wherein said second cushion means is normally biased by said leaf spring means to slope upwardly of said adjacent end of said first cushion means in said upper position and is movable through an intermediate position generally level with said first cushion means upon travel toward said lower position.

47. The table of claim 46, wherein said external force may comprise said patient's weight carried by second cushion means and a force applied outwardly of said ball joint to pivot said second cushion means from said intermediate position toward said lower position.

48. The table of claim 45, including hand grip means on opposite sides of said first cushion means for rocking said cushion means to pivot about said longitudinal axis.

49. The table of claim 45, wherein said first cushion means is manually rockable in opposite directions about said longitudinal pivot axis between oppositely tilted positions, and locking means for securing said first cushion means in a selected position between said oppositely tilted positions.

50. The table of claim 49, wherein said locking means includes a plurality of operating handles disposed on opposite sides of said table for operator axis.

51. The table of claim 49, wherein said locking means includes a clamping assembly on said base means operable to clamp and release said first cushion means for rocking movement between said tilted positions toward a selected position.

52. The table of claim 51, wherein said locking means includes an operating shaft with end portions projecting outwardly of opposite sides of said base means, one of said handles secured to each of said end portions and aligned to release said clamping assembly on downward travel of either handle.

53. The table of claim 51, wherein said clamping means includes a pair of clamping jaws and an over-center toggle mechanism connected to move at least one of said jaws to a clamping position when a toggle link of said mechanism is moved past an over-center alignment relative to one jaw.

54. The table of claim 49, wherein said mounting means includes a plurality of arcuately shaped rods extending transversely of said first cushion means at longitudinally spaced apart positions, said locking means includes a block mounted on said base means and having an opening therein through which one of said arcuate rods extends, and means for holding said one rod in engagement with said block.

55. The table of claim 54, wherein said holding means comprises a pair of members pivotally mounted on said block and having cooperating recesses in the opposing faces thereof, and a toggle member positioned in said recesses and adapted upon rotation of one of said members to force the other member into engagement with said one rod and said one rod into engagement with said block.

56. The table of claim 55, which includes a shaft mounted on said block for rotation about a horizontal axis, said one member being connected to and rotatable with said shaft, and an arm connected to said shaft outside said block for rotating said shaft and said arm member.

57. The table of claim 56, wherein said recesses are shaped to limit movement of said arm from a generally horizontal clamping position in which said other member holds said one rod in engagement with said block to a lower released position in which said one rod is free to move within said opening in said block.

58. The table of claim 57 wherein said opposed recesses are generally V-shaped and said toggle member comprises a flat metal bar positioned edgewise in said V-shaped recesses.

59. The table of claim 58 wherein the sides of said V-shaped recesses cooperate with said metal bar to limit movment of said arm to movement between said generally horizontal position and said lower position.

* * * * *